United States Patent [19]

LaBelle et al.

[11] Patent Number: 5,350,760
[45] Date of Patent: Sep. 27, 1994

[54] AZA-5,5-FUSED HETROCYCLIC ACIDS AS LEUKOTRIENE ANTAGONISTS

[75] Inventors: Marc LaBelle, Ile Perrot, Canada; Yibin Xiang, Lexington, Mass.; Claude Dufresne, Dollard-des-Ormeaux; Michel Belley, Pierrefonds, both of Canada

[73] Assignee: Merck Frosst Canada, Inc., Kirkland, Canada

[21] Appl. No.: 101,882

[22] Filed: Aug. 4, 1993

[51] Int. Cl.$^5$ .............. C07D 513/04; C07D 498/04; A61K 31/42; A61K 31/425
[52] U.S. Cl. .................... 514/367; 514/375; 548/153; 548/218
[58] Field of Search ............... 548/153, 218; 514/367, 514/375

[56] References Cited

U.S. PATENT DOCUMENTS 4,794,188 12/1988 Musser et al. ............... 546/152
5,037,840 8/1991 Young et al. ............... 514/367

FOREIGN PATENT DOCUMENTS

0367235A1 5/1990 European Pat. Off. .

*Primary Examiner*—Joseph Paul Brust
*Assistant Examiner*—MarySusan H. Gabilan
*Attorney, Agent, or Firm*—Robert J. North; Melvin Winokur

[57] ABSTRACT

Compounds having the formula I:

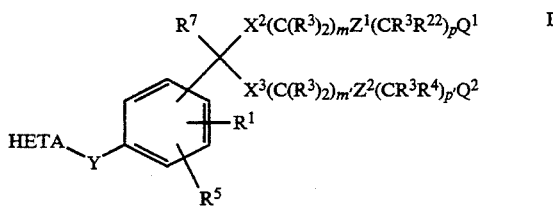

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

14 Claims, No Drawings

AZA-5,5-FUSED HETEROCYCLIC ACIDS AS LEUKOTRIENE ANTAGONISTS

BACKGROUND OF THE INVENTION

The leukotrienes constitute a group of locally acting hormones, produced in living systems from arachidonic acid. The major leukotrienes are Leukotriene $B_4$ (abbreviated at $LTD_4$), $LTC_4$, $LTD_4$ and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

U.S. Pat. No. 4,957,932, Young et al. discloses compounds similar to those of formula 1 as leukotriene antagonists and inhibitors of leukotriene biosynthesis. The present compounds differ from Young's primarily in having a different heterocyclic ring on the left side of the structure. Fujikawa describes the thieno[2,3-b]-pyridine 2 in EP 367,235 but the point of attachment and the nature of the principal substituent are different from the present compounds. Musser et al. describe compound 3 in U.S. Pat. No. 4,794,188 as being lipoxygenase inhibitors and possessing anti-inflammatory and anti-allergic activities. However, compound 3 differs from the present compounds principally in that $Ar_1$ is different from our HETA grouping. Thus, the compounds of the present invention are novel.

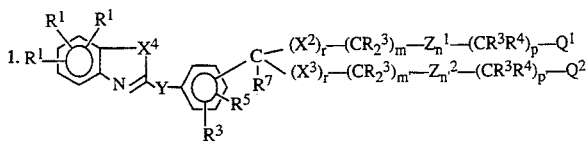

Young, et al. U.S. Pat No. 4,957,932

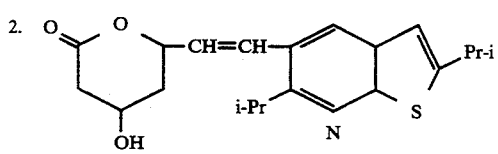

Fujikawa EP 367,235

Ar₁—X—Ar—Z—(R)ₙ'     3.

Musser et al. U.S. Pat. No. 4,794,188.

SUMMARY OF THE INVENTION

The present invention relates to aza-5,5-fused heterocyclic acids having activity as leukotriene antagonists, to methods for their preparation, and to methods and pharmaceutical formulations for using s these compounds in mammals (especially humans).

Because of their activity as leukotriene antagonists, the compounds of the present invention are useful as anti-asthmatic, anti-allergic, anti-inflammatory and cytoprotective agents. They are also useful in treating angina, cerebral spasm, glomerular nephritis, hepatitis, endotoxemia, uveitis, and allograft rejection.

DETAILED DESCRIPTION OF THE INVENTION

By this invention there is provided compounds of Formula I:

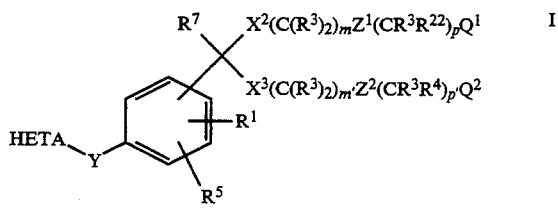

wherein:

$R^1$ is H or $R^2$;

$R^2$ is lower alkyl, lower alkenyl, lower alkynyl, fluoro lower alkyl, $Ph(R^{26})_2$, $CH_2Ph(R^{26})_2$, $CH_2CH_2Ph(R^{26})_2$ or two $R^2$ groups joined to the same carbon can form a ring of up to 8 members containing up to 2 heteroatoms chosen from O,S,N;

$R^3$ is H or $R^2$;

$R^4$ is $R^3$, halogen, $-NO_2$, $-CN$, $-CF_3$, $-OR^3$, $N(R^3)_2$, $NR^3COR^7$, $-SR^2$, $S(O)R^2$ or $S(O)_2R^2$;

$CR^3R^{22}$ can be the radical of a conventional amino acid;

$R^5$ is H, halogen, $-NO_2$, $-N_3$, $-CN$, $-SR^2$, $-S(O)R^2$, $S(O)_2R^2$, $-N(R^{10})_2$, $-OR^3$, $-COR^3$, lower alkyl or fluoro lower alkyl;

$R^6$ is $-(CH_2)_s-C(R^7)_2-(CH_2)_s-R^8$ or $-CH_2CON(R^{20})_2$;

$R^7$ is H or lower alkyl;

$R^8$ is A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or B) the radical $W-R^9$;

$R^9$ contains up to 21 carbon atoms and is (1) a hydrocarbon radical or (2) an acyl radical of an organic acyclic or monocyclic carboxylic acid containing not more than 1 heteroatom in the ting;

$R^{10}$ is $R^{12}$;

$R^{11}$ is lower alkyl, $-COR^{14}$, $Ph(R^{26})_2$, $CH_2Ph(R^{26})_2$, $CH_2CH_2Ph(R^{26})_2$;

$R^{12}$ is H, $R^{11}$, or two $R^{12}$ groups joined to the same N may form a saturated ring of 5 or 6 members containing up to two heteroatoms chosen from O, S or N;

$R^{13}$ is lower alkyl, lower alkenyl, lower alkynyl, $-CF_3$, $Ph(R^{26})_2$, $CH_2Ph(R^{26})_2$ or $CH_2CH_2Ph(R^{26})_2$;

$R^{14}$ is H or $R^{13}$;

$R^{15}$ is H or $R^{11}$;

$R^{16}$ is H, lower alkyl, or OH;

$R^{17}$ is lower alkyl, lower alkenyl, lower alkynyl, $Ph(R^{26})_2$, $CH_2Ph(R^{26})_2$ or $CH_2CH_2Ph(R^{26})_2$;

$R^{18}$ is $R^{13}$;

$R^{19}$ is H, lower alkyl, lower alkenyl, lower alkynyl, —$CF_3$, Ph, $CH_2Ph$, or $CH_2CH_2Ph$;

$R^{20}$ is H, lower alkyl, $Ph(R^{26})_2$, $CH_2Ph(R^{26})_2$, $CH_2CH_2Ph(R^{26})_2$ or two $R^{20}$ groups joined to the same N can form a saturated ring of 5 or 6 members containing up to two heteroatoms chosen from O, S or N;

$R^{21}$ is H or $R^{17}$;

$R^{22}$ is $R^4$, $CHR^7OR^3$ or $CHR^7SR^2$;

$R^{23}$, $R^{24}$ and $R^{25}$ are each independently H, lower alkyl, —CN, —$CF_3$, $COR^3$, $CO_2R^7$, $CON(R^{20})_2$, $OR^3$, $SR^2$, $S(O)R^2$, $S(O)_2R^2$, $N(R^{12})_2$, halogen, or an electron pair;

$R^{26}$ is H, lower alkyl, —$COR^7$, $CO_2R^7$, $CON(R^{19})_2$, —CN, $CF_3$, $NO_2$, $SCF_3$, $SR^{27}$, $OR^{28}$, $N(R^{28})_2$, or halogen;

$R^{27}$ is lower alkyl, phenyl or benzyl;

$R^{28}$ is H, $R^{27}$ or $COR^7$, or two $R^{28}$ groups joined to the same N can form a saturated ring of 5 or 6 members comprising carbon atoms and up to 2 heteroatoms chosen from O, S or N;

m and m' are independently 0–8;

p and p' are independently 0–8;

m+p is 1–10 when $X^2$ is O, S, S(O), or $S(O)_2$ and $Z^1$ is a bond;

m+p is 0–10 when $Z^1$ is $HET(R^{23}R^{24}R^{25})$;

m+p is 0–10 when $X^2$ is $CR^3R^{16}$;

m'+p' is 1–10 when $X^3$ is O, S, S(O), or $S(O)_2$ and $Z^2$ is a bond;

m'+p' is 0–10 when $Z^2$ is $HET(R^{23}R^{24}R^{25})$;

m'+p' is 0–10 when $X^3$ is $CR^3R^{16}$;

s is 0–3;

$Q^1$ is tetrazol-5-yl, —$CO_2R^3$, —$CO_2R_6$, —$CONHS(O)_2R^{13}$, —CN, —$CON(R^{20})_2$, $NR^{21}S(O)_2R^{13}$, —$NR^{21}CON(R^{20})_2$, —$NR^{21}COR^{14}$, $OCON(R^{20})_2$, —$COR^{19}$, —$S(O)R^{18}$, —$S(O)_2R^{18}$, —$S(O)_2N(R^{12})_2$, —$NO_2$, $NR^{21}CO_2R^{17}$, —$C(N(R^{12})_2)=NR^{21}$, —$C(R^{19})=NOR$, $C(R^3)_2OR^3$; or if $Q^1$ is $CO_2H$ and $R^{22}$ is —OH, —SH, $CHR^7OH$ or —$NHR^3$, then $Q^1$ and $R^{22}$ and the carbons through which they are attached can form a heterocyclic ring by loss of water;

$Q^2$ is H, $OR^{15}$, lower alkyl, fluoro lower alkyl, halogen or $Q^1$;

W is O, S, or $NR^3$;

$X^1$ is O, S, —S(O)—, —$S(O)_2$—, —$NR^3$, —$C(R^3)_2$—, or a bond;

$X^2$ and $X^3$ are independently O, S, S(O), $S(O)_2$, $CR^3R^{16}$ or a bond;

Y is —$CR^3=CR^3$—, —$C(R^3)_2$—$X^1$—, —$X^1$—$C(R^3)_2$—, —$C(R^3)_2$—$X^1$—$C(R^3)_2$—, —C≡C—, —CO—, —$NR^3CO$—, —$CONR^3$—, O, S, or $NR^3$;

$Z^1$ and $Z^2$ are independently $HET(R^{23}R^{24}R^{25})$ or a bond;

HET is the diradical of benzene, pyridine, furan, thiophene or 1,2,5-thiadiazole;

HETA is $HE^1$ or $HE^2$, $HE^1$ is

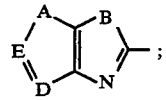

$HE^2$ is

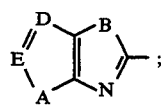

each A is O, S, $S(O)_2$;

each B is independently O, S, S(O) or $S(O)_2$;

each D is independently N or $CR^4$;

E is $CR^4$ except when D is N, where E is $CR^3$; or a pharmaceutically acceptable salt thereof.

Preferred compounds of formula I are those of Formula Ia:

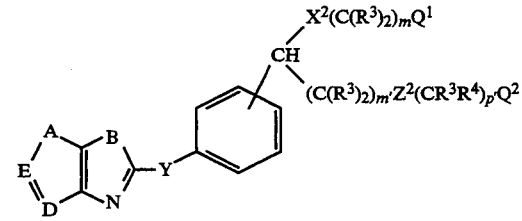

wherein:

A is S or O;

B is S or O;

$R^4$ is H, halogen, CN, $CF_3$, $S(O)_2R^2$;

m and m' are independently 1–6;

p' is 0 or 1;

$Q^1$ is $CO_2R^3$, $CO_2R^6$, —$CONHS(O)_2R^{13}$, tetrazol-5-yl, $C(R^3)_2OH$;

$Q^2$ is $C(R^3)_2OH$, halogen, lower alkyl, $COR^{19}$;

$X^2$ is S or O;

Y is —CH=CH—, —$CH_2$—O—, —$CH_2$—$CH_2$—, —C≡C— or —$CH(CH_2)CH$—;

$Z^2$ is HET $(R^{23}R^{24})$;

HET is a diradical of benzene or thiophene;

and the remaining substituents are as defined for Formula I.

A group of most preferred compounds is described by formula Ib:

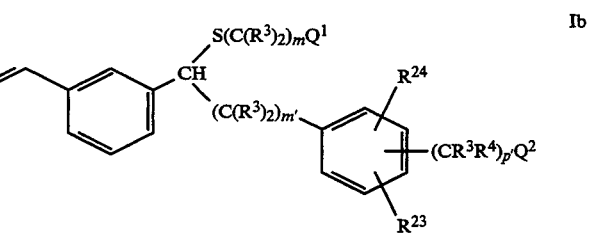

wherein:

R³ is H, lower alkyl, or two R³ joined to the same carbon may form a ring from 3 to 6 members, optionally containing one oxygen or sulfur;

R⁴ is H, halogen, —CN, —CF₃, —S(O)₂R²;

R²³ and R²⁴ are independently H, halogen or lower alkyl;

m and m' are independently 1–5;

p' is 0 or 1;

Q¹ is —CO₂R³, tetrazol-5-yl, —CONHS(O)₂R¹³;

Q² is C(R³)₂OH;

Definitions

The following abbreviations have the indicated meanings:

Ac=acetyl
AIBN=2.2_-azobisisobutyronitrile
Bn=benzyl
DHP=2.3-dihydro-4H-pyran
DIBAL=diisobutylaluminum hydride
DIPHOS=1,2-bis(diphenylphosphino)ethane
DMAP=4-(dimethylamino)pyridine
DMF=N,N-dimethylformamide
DMSO=dimethyl sulfoxide
Et₃N=triethylamine
Fur=furandiyl
KHMDS=potassium hexamethyldisilazane
LDA=lithium diisopropylamide
Ms=methanesulfonyl=mesyl
MsO=methanesulfonate=mesylate
NBS=N-bromosuccinimide
NCS=N-chlorosuccinimide
NIS=N-iodosuccinimide
NSAID=non-steroidal anti-inflammatory drug
PCC=pyridinium chlorochromate
PDC=pyridinium dichromate
Ph=phenyl
phe=benzenediyl
PPTS=pyridinium p-toluenesulfonate
PTSA=p-toluenesulfonic acid
Pye=pyridinediyl
r.t.=room temperature
rac.=racemic
Tdz=1,2,5-thiadiazol-3,4-diyl
Tf=trifluoromethanesulfonyl=triflyl
TfO=trifluoromethanesulfonate=triflate
Th=2- or 3-thienyl
THF=tetrahydrofuran
Thi=thiophenediyl
THP=tetrahydropyran-2-yl
TLC=thin layer chromatography
Ts=potoluenesulfonyl=tosyl
TsO=p-toluenesulfonate=tosylate
Tz=1H (or 2H)-tetrazol-5-yl
C₃H₅=allyl

Alkyl Group Abbreviations

Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl The terms alkyl, alkenyl, and alkynyl mean linear, branched and cyclic structures and combinations thereof.

The term "alkyl" includes "cycloalkyl" and "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4propyl-nonyl, and the like.

"Lower alkyl" includes "lower cycloalkyl" and means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Fluoro lower alkyl" means lower alkyl groups in which one or more hydrogen is replaced by fluorine. Examples are —CF₃, —CH₂CH₂F, —CH₂CF₃, c—Pr—F₅, c—Hex—F₁₁ and the like.

"Cycloalkyl" includes "lower cycloalkyl" and means a hydrocarbon, containing one or more rings of from 3 to 12 carbon atoms, with the hydrocarbon having up to a total of 20 carbon atoms. Examples of cycloalkyl groups are cyclopropyl, cyclopentyl, cycloheptyl, aldamantyl, cyclododecylmethyl, 2-ethyl-1-bicyclo[4.4.0]decyl and the like.

"Lower cycloalkyl" means a hydrocarbon containing one or more tings of from 3 to 7 carbon atoms, with the hydrocarbon having up to a total of 7 carbon atoms. Examples of lower cycloalkyl groups are cyclopropyl, cyclopropylmethyl, cyclobutyl, 2-cyclopentylethyl, cycloheptyl, bicyclo[2.2.1]hept-2-yl and the like.

The term "alkenyl" includes "cycloalkenyl" and "lower alkenyl" and means alkenyl groups of 2 to 20 carbon atoms. Examples of alkenyl groups include allyl, 5-decen-1-yl, 2-dodecen-1-yl, and the like.

"Lower alkenyl" includes "lower cycloalkenyl" and means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl and the like.

"Cycloalkenyl" includes "lower cycloalkenyl" and means alkenyl groups of 3 to 20 carbon atoms, which include a ring of 3 to 12 carbon atoms, and in which the alkenyl double bond may be located anywhere in the structure. Examples of cycloalkenyl groups are cyclopropen-1-yl, cyclohexen-3-yl, 2-vinyladamant-1-yl, 5-methylenedodec-1-yl, and the like.

"Lower cycloalkenyl" means alkenyl groups of 3 to 7 carbon atoms, which include a ring of 3 to 7 carbon atoms and in which the double bond may be located anywhere in the structure. Examples of lower cycloalkenyl groups are cyclopropen-1-yl, cyclohexen-3-yl, 2-cyclopentylethen-1-yl and the like.

The term "alkynyl" includes "cycloalkynyl" and "lower alkynyl" and means alkynyl groups of 2 to 20 carbon atoms. Examples of alkynyl groups are ethynyl, 2-pentadecyn-1-yl, 1-eicosyn-1-yl, and the like.

"Lower alkynyl" includes "lower cycloalkynyl" and means alkynyl groups of 2 to 7 carbon atoms. Examples of lower alkynyl groups include ethynyl, propargyl, 3-methyl-1-pentynyl, 2-heptynyl and the like.

"Cycloalkynyl" includes "lower cycloalkynyl" and means alkynyl groups of 5 to 20 carbon atoms, which include a ring of 3 to 20 carbon atoms. The alkynyl triple bond may be located anywhere in the group, with the proviso that if it is within a ring, such a ring must be 10 members or greater. Examples of cycloalkynyl are cyclododecyn-3-yl, 3-cyclohexyl-1-propyn-1-yl, and the like.

"Lower cycloalkynyl" means alkynyl groups of 5 to 7 carbon atoms which include a ring of 3 to 5 carbon atoms. Examples of lower cycloalkynyl are cyclopropylethynyl, 3-(cyclobutyl)-1-propynyl and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

"Lower alkylsulfonyl" means alkylsulfonyl groups of from 1 to 7 carbon atoms of a straight, branched or cyclic configuration. Examples of lower alkylsulfonyl groups are methylsulfonyl, 2-butylsulfonyl, cyclohexylmethylsulfonyl, etc. By way of illustration the 2-butylsulfonyl group signifies —$S(O)_2CH(CH_3)CH_2CH_3$.

The term "alkylcarbonyl" includes "lower alkylcarbonyl" and means alkylcarbonyl groups of 1 to 20 carbon atoms of a straight, branched or cyclic configuration. Examples of alkylcarbonyl groups are formyl, 2-methylbutanoyl, octadecanoyl, 11-cyclohexylundecanoyl and the like. Thus, the 11-cyclohexylundecanoyl group is c—$Hex(CH_2)_{10}$—CO—.

"Lower alkylcarbonyl" means alkylcarbonyl groups of from 1 to 8 carbon atoms of a straight, branched or cyclic configuration. Examples of lower alkylcarbonyl groups are formyl, 2-methylbutanoyl, cyclohexylacetyl, etc. By way of illustration, the 2-methylbutanoyl groups signifies —$COCH(CH_3)CH_2CH_3$.

The term $Ph(R^{26})_2$ indicates a phenyl group substituted with two $R^{26}$ substituents.

Halogen includes F, Cl, Br, and I.

It is intended that the definitions of any substituent (e.g., $R^{12}$, $Ph(R^{26})_2$, etc.) in a particular molecule be independent of its definitions elsewhere in the molecule. Thus, —$N(R^{12})_2$ represents —NHH, —$NHCH_3$, —$NHC_6H_5$, etc.

The rings formed when two $R^2$ groups join include cyclopropane, cyclobutane, cyclopentane, cyclohexane, cycloheptane, cyclooctane, oxetane, tetrahydrofuran, tetrahydropyran, thiooxetane, tetrahydrothiophene, tetrahydrothiopyran, pyrrolidine, piperidine, morpholine, thiamorpholine, piperazine and the N-methyl derivatives of the nitrogen containing heterocycles.

The heterocycles formed when two $R^{10}$, $R^{12}$, $R^{20}$ or $R^{28}$ groups join through N include pyrrolidine, piperidine, morpholine, thiamorpholine, piperazine, and N-methylpiperazine.

When $Q^1$ and $R^{22}$ and the carbons through which they are attached form a ring, the rings thus formed include lactones, lactams, and thiolactones.

The prodrug esters of Q (i.e., when Q=$COOR^6$) are intended to include the esters such as are described by Saari et al., J. Med. Chem., 21, No. 8, 746–753 (1978), Sakamoto et al, Chem. Pharm. Bull., 32, No. 6, 2241–2248 (1984) and Bundgaard et al., J. Med. Chem., 30, No. 3, 451–454 (1987). Within the definition of $R^8$, some representative monocyclic or bicyclic heterocyclic radicals are:

2,5-dioxo-1-pyrrolidinyl,
(3-Pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl,
piperazin-1-yl.

The term "standard amino acid" means the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine. (See F.H.C. Crick, Symposium of the Society of Experimental Biology, 1958 (12), p. 140).

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) hepatitis resulting from chemical. immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal hilum. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most s preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carder and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |
| Tablet | mg/tablet |
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |
| Aerosol | Per canister |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations with Other Drugs

In addition to the compounds of Formula I, the pharmaceutical compositions of the present invention can also contain other active ingredients, such as cyclooxygenase inhibitors, nonsteroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) propionic acid derivatives;
(2) acetic acid derivatives;
(3) fenamic acid derivatives;
(4) oxicams; and
(5) biphenylcarboxylic acid derivatives, or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO—Na$^+$ or —CH$_2$CH$_2$COO—Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are nonnarcotic analgesics/non-steroidal anti-inflammatory drugs having a free —CH$_2$COOH group (which optionally can be in the form of a pharmaceutically acceptable salt group, e.g. —CH$_2$COO—Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are nonnarcotic analgesics/non-steroidal anti-inflammatory drugs which contain the basic structure:

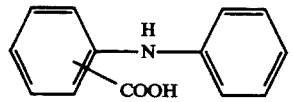

which can bear a variety of substituents and in which the free —COOH group can be in the form of a pharmaceutically acceptable salt group, e.g., —COO—Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

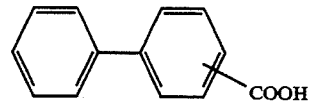

which can bear a variety of substituents and in which the free —COOH group can be in the form of a pharmaceutically acceptable salt group, e.g., —COO—Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non narcotic analgesics/non-steroidal anti-inflammatory drugs which have the general formula:

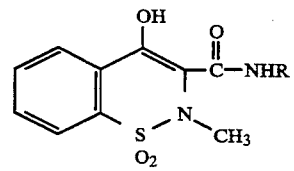

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tifiamizole, timegadine, tolpadol, tryptamid, and ufenamate.

The following NSAIDs, designated by company code number (see e.g., Pharmaprojects), may also be used: 0156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS21;31, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, fiurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24,1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981 ), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, 316, 126–131 (1985), and the like. Each of the references referred to in this paragraph is hereby incorporated herein by reference.

Other advantageous pharmaceutical compositions comprise s the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

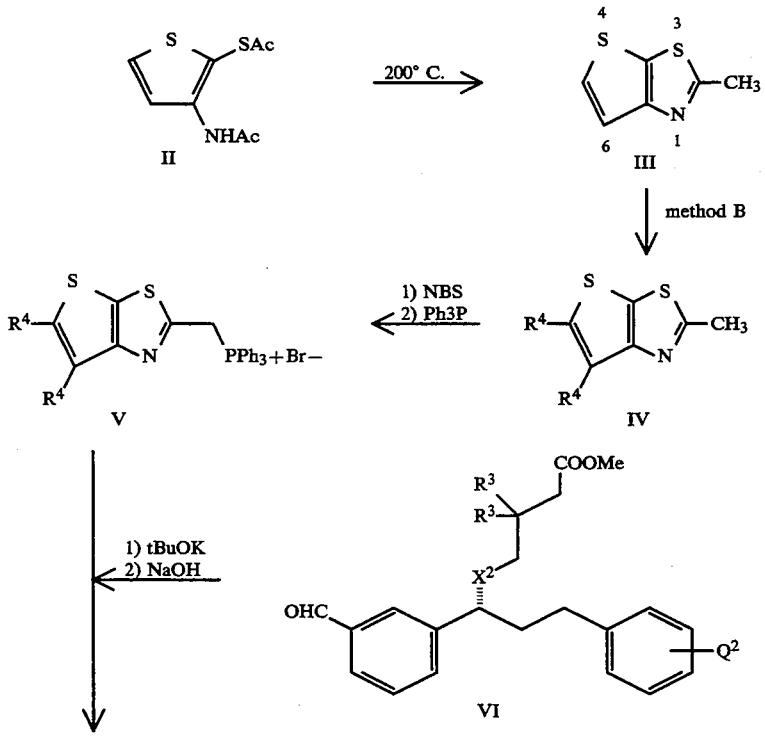

METHOD A

METHOD A
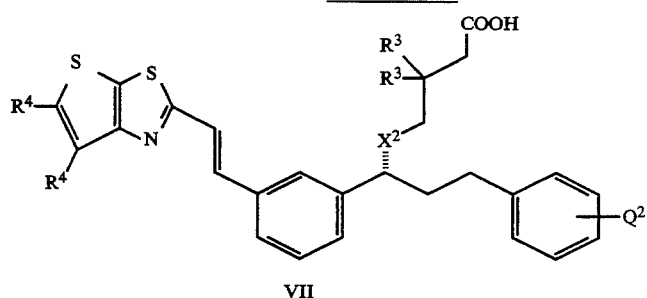
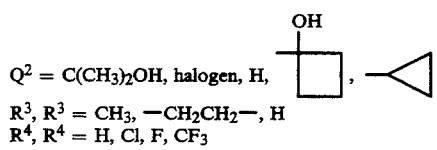
$Q^2$ = C(CH$_3$)$_2$OH, halogen, H, [cyclobutanol], cyclopropyl,
$R^3, R^3$ = CH$_3$, —CH$_2$CH$_2$—, H
$R^4, R^4$ = H, Cl, F, CF$_3$
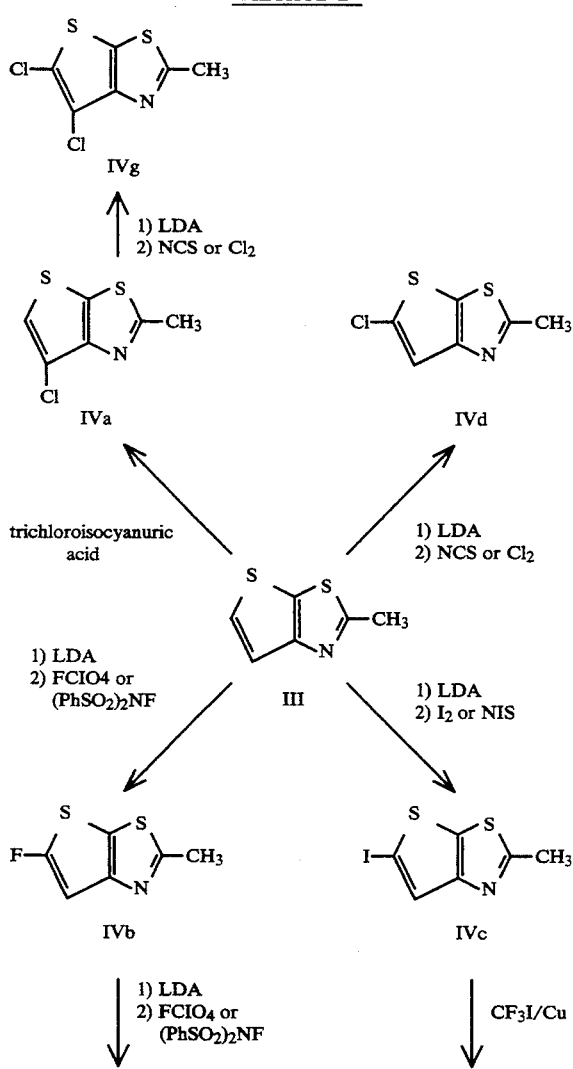
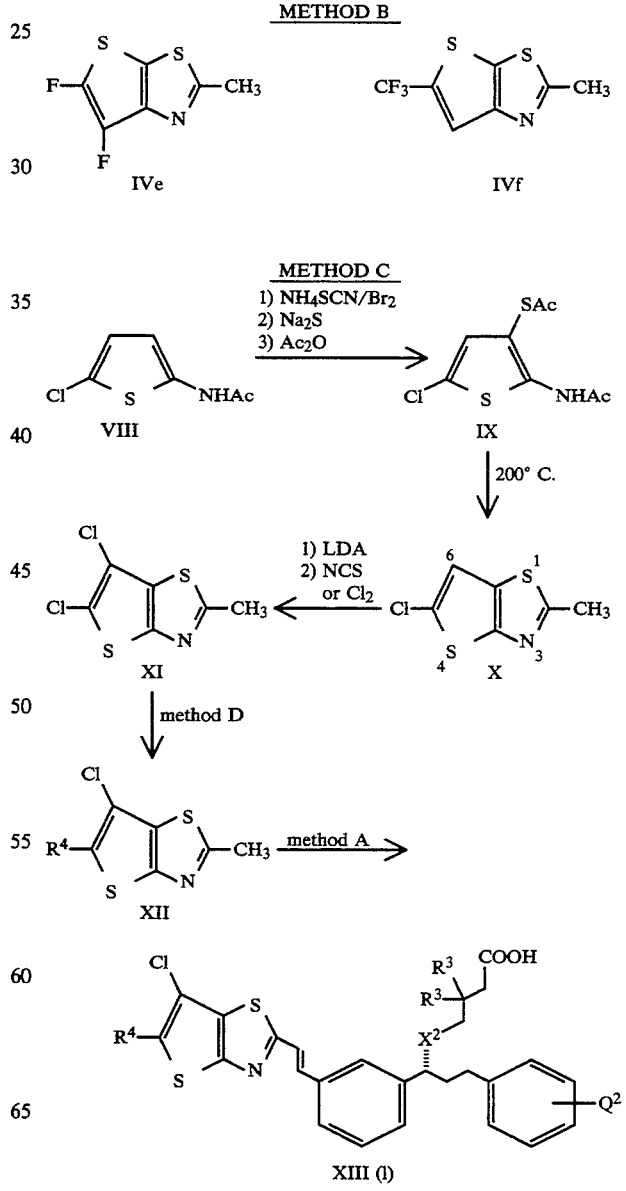

-continued
METHOD C

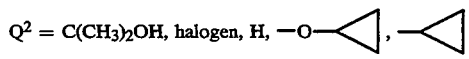

$R^3, R^3 = CH_3, -CH_2CH_2-, H$
$R^4 = H, Cl, F, CF_3$, cyclopropane

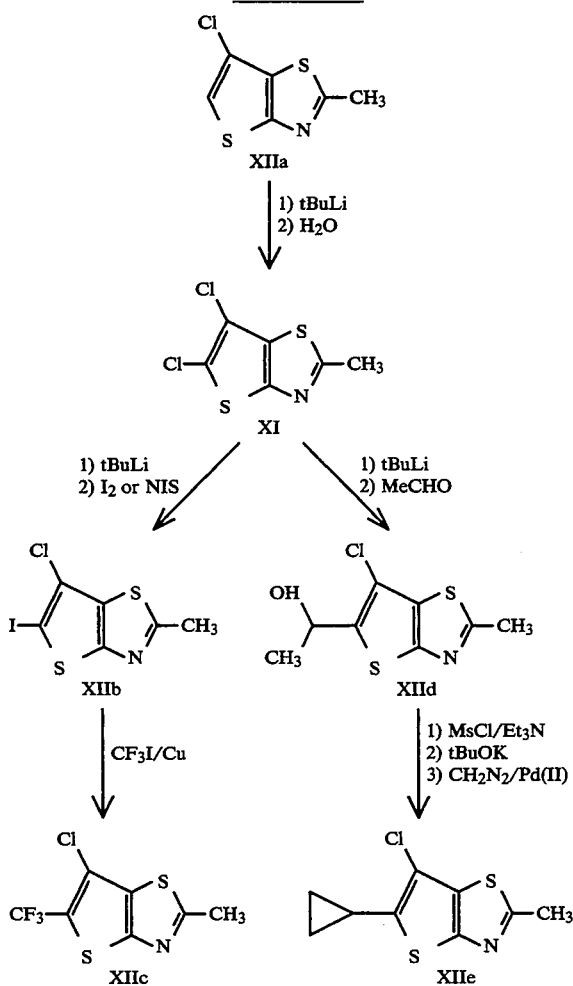

Methods of Synthesis

Compounds of the present invention can be prepared according to the above-illustrated methods hereby further described.

Method A

Diacetate II, prepared from tetrahydrothiophen-3-one according to literature procedures (C. Paulmier, Bull. Soc. Chim. Fr. (1979) 11,592), is heated in toluene at 200° C. to give thienothiazole III. III is converted to various substituted thienothiazoles IV by reactions described in method B. Treatment of IV with N-bromosuccinimide in carbon tetrachloride, followed by reaction with triphenylphosphine affords phosphonium salt V. Wittig reaction between V and aldehyde VI in the presence of base, such as potassium tert-butoxide, or potassium bis(trimethylsilyl)amide, followed by hydrolysis with aqueous sodium hydroxide gives acid VII. Examples of aldehyde VI are described in U.S. Pat. No. 5,104,882 (Methods D and I), in EP 480,717 (Method H), as well as in the present examples.

Method B

Treatment of thienothiazole III with trichloroisocyanuric acid gives IVa.

Deprotonation of III with strong base, such as LDA, affords the thienothiazolo5-yl anion, which reacts with various electrophiles to give different 5-substituted thienothiazoles IV,: e.g. reaction with N-fluoro-bis(benzenesulfonyl)amide, or fluorine perchlorate to give IVb; reaction with iodine or N-iodosuccinimide to give IVc; or reaction with chlorine or N-chlorosuccinimide to give IVd.

Treatment of IVc with iodotrifluoromethane and copper in DMF gives IVf.

Treatment of IVa with strong base, such as LDA, followed by reaction with N-chlorosuccinimide or chlorine gives IVg.

Treatment of IVb with LDA, followed by reaction with a fluorine perchlorate or N-fluoro-bis(benzenesulfonyl)amide gives IVe.

Method C

Thiophene amide VIII, prepared according to literature procedures (H. Gupte and D. N. Patkar, J. Indian Chem. Soc. 56, (1979) 839), is converted to IX by the following sequence: 1) thiocyanation with ammonium thiocyanate and bromine; 2) hydrolysis with aqueous sodium sulfide, and 3) reaction with acetic anhydride. Heating of IX in toluene at 200° C. affords thienothiazole X. Treatment of X with a strong base, such as LDA, followed by reaction with N-chlorosuccinimide or chlorine gives 5,6-dichlorothienothiazole XI.

XI is converted to various 5,6-disubstituted thienothiazoles XII by the reactions described in Method D. Finally, XII is transformed into acid XIII by the procedures described in Method A.

Method D

Lithiation of dichlorothienothiazole XI, obtained in method C, with tert-butyl lithium gives 5-lithiothienothiazole, which reacts with various electrophiles to give different 5,6-disubstituted thienothiazoles: e.g. reaction with iodine or N-iodosuccinimide to give XIIb; reaction with acetaldehyde to give XIId; or reaction with water to give XIIa.

Treatment of XIIb with iodotrifluoromethane and copper in DMF gives XIIc.

XIId is converted to XIIe by the following sequence: 1) mesylation with mesyl chloride and triethylamine; 2) elimination of methanesulfonic acid with a strong base, such as potassium tert-butoxide; and 3) cyclopropanation with diazomethane in the presence of a palladium (II) catalyst.

Representative Compounds

Table I and Table 2 illustrate compounds which are representative of the present invention. In these tables, $Y^1$ stands for $-X^2(C(R^3)_2)_m{'}Z^1(C(R^3R^{22})_pQ^1$ and $W^1$ stands for $-X^3(C(R^3)_2)_m{'}Z^2(CR^3R^4)_p{'}Q^2$ from Formula I.

TABLE 1

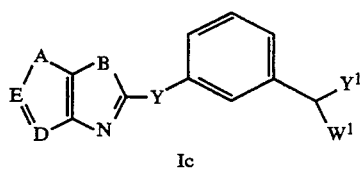

Ic

| EX | A | B | D | E | Y | Y¹ | W¹ |
|----|---|---|---|---|---|----|----|
| 1  | S | S | CCl | CH   | CH=CH | SCH$_2$(1,1-c-Pr)CH$_2$CO$_2$H | (CH$_2$)$_2$(1,2-phe)C(CH$_3$)$_2$OH |
| 2  | S | S | CCl | CCl  | CH=CH | SCH$_2$(1,1-c-Pr)CH$_2$CO$_2$H | (CH$_2$)$_2$(1,2-phe)C(CH$_3$)$_2$OH |
| 3  | S | S | CH  | CCl  | CH=CH | SCH$_2$(1,1-c-Pr)CH$_2$CO$_2$H | (CH$_2$)$_2$(1,2-phe)C(CH$_3$)$_2$OH |
| 4  | S | O | CH  | CCl  | CH=CH | SCH$_2$(1,1-c-Pr)CH$_2$CO$_2$H | (CH$_2$)$_2$(1,2-phe)C(CH$_3$)$_2$OH |
| 5  | S | S | CH  | CF   | CH=CH | SCH$_2$(1,1-c-Pr)CH$_2$CO$_2$H | (CH$_2$)$_2$(1,2-phe)C(CH$_3$)$_2$OH |
| 6  | S | S | CF  | CF   | CH=CH | SCH$_2$(1,1-c-Pr)CH$_2$CO$_2$H | (CH$_2$)$_2$(1,2-phe)C(CH$_3$)$_2$OH |
| 7  | S | S | CH  | CCF$_3$ | CH=CH | SCH$_2$(1,1-c-Pr)CH$_2$CO$_2$H | (CH$_2$)$_2$(1,2-phe)C(CH$_3$)$_2$OH |
| 9  | S | S | CCl | CH   | CH=CH | SCH$_2$(1,1-c-Pr)CH$_2$CO$_2$H | (CH$_2$)$_2$(1,3-phe)C(CH$_3$)$_2$OH |
| 10 | O | S | CH  | CCl  | CH=CH | SCH$_2$(1,1-c-Pr)CH$_2$CO$_2$H | (CH$_2$)$_2$(1,2-phe)C(CH$_3$)$_2$OH |
| 11 | S | S | CCl | CF   | CH=CH | SCH$_2$(1,1-c-Pr)CH$_2$CO$_2$H | (CH$_2$)$_2$(1,2-phe)C(CH$_3$)$_2$OH |
| 12 | S | S | CCl | CCl  | CH=CH | SCH$_2$(1,1-c-Pr)CH$_2$CO$_2$H | (CH$_2$)$_2$(1,4-phe)c-Pr |
| 13 | S | S | CCl | CH   | CH=CH | SCH$_2$(1,1-c-Pr)CH$_2$CO$_2$H | (CH$_2$)$_2$(1,4-phe)c-Pr |
| 14 | S | S | CH  | CCl  | CH=CH | SCH$_2$(1,1-c-Pr)CH$_2$CO$_2$H | (CH$_2$)$_2$(1,4-phe)c-Pr |
| 15 | S | S | CH  | CCl  | CH=CH | SCH$_2$(1,1-c-Pr)CH$_2$CO$_2$H | (CH$_2$)$_2$(1,4-phe)-O-c-Pr |
| 16 | S | S | CH  | CF   | CH=CH | SCH$_2$(1,1-c-Pr)CH$_2$CO$_2$H | (CH$_2$)$_2$(1,4-phe)c-Pr |
| 17 | S | S | CF  | CF   | CH=CH | SCH$_2$(1,1-c-Pr)CH$_2$CO$_2$H | (CH$_2$)$_2$(1,4-phe)c-Pr |
| 18 | S | S | CH  | CCF$_3$ | CH=CH | SCH$_2$(1,1-c-Pr)CH$_2$CO$_2$H | (CH$_2$)$_2$(1,4-phe)c-Pr |
| 20 | S | O | CCl | CH   | CH=CH | SCH$_2$(1,1-c-Pr)CH$_2$CO$_2$H | (CH$_2$)$_2$(1,4-phe)c-Pr |
| 21 | S | O | CH  | CCl  | CH=CH | SCH$_2$(1,1-c-Pr)CH$_2$CO$_2$H | (CH$_2$)$_2$(1,4-phe)c-Pr |
| 22 | S | O | CF  | CF   | CH=CH | SCH$_2$(1,1-c-Pr)CH$_2$CO$_2$H | (CH$_2$)$_2$(1,4-phe)c-Pr |

TABLE 2

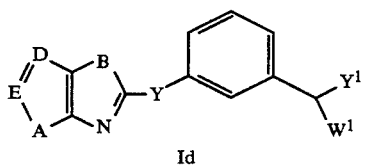

Id

| EX | A | B | D | E | Y | Y¹ | W¹ |
|----|---|---|---|---|---|----|----|
| 23 | S | S | CCl | CH     | CH=CH | SCH$_2$(1,1-c-Pr)CH$_2$CO$_2$H | (CH$_2$)$_2$(1,2-phe)C(CH$_3$)$_2$OH |
| 24 | S | S | CCl | CCF$_3$ | CH=CH | SCH$_2$(1,1-c-Pr)CH$_2$CO$_2$H | (CH$_2$)$_2$(1,2-phe)C(CH$_3$)$_2$OH |
| 25 | S | S | CCl | Cc—Pr  | CH=CH | SCH$_2$(1,1-c-Pr)CH$_2$CO$_2$H | (CH$_2$)$_2$(1,2-phe)C(CH$_3$)$_2$OH |
| 26 | S | S | CCl | Cc—Pr  | CH=CH | SCH$_2$C(CH$_3$)$_2$CH$_2$CO$_2$H | (CH$_2$)$_2$(1,2-phe)C(CH$_3$)$_2$OH |
| 27 | S | S | CCl | Cc—Pr  | CH=CH | SCH$_2$C(CH$_3$)$_2$CH$_2$CO$_2$H | (CH$_2$)$_2$(1,4-phe)c-Pr |
| 28 | S | S | CCl | Cc—Pr  | CH=CH | SCH$_2$(1,1-c-Pr)CH$_2$CO$_2$H | (CH$_2$)$_2$(1,4-phe)Br |
| 29 | S | S | CCl | Cc—Pr  | CH=CH | SCH$_2$(1,1-c-Pr)CH$_2$CO$_2$H | (CH$_2$)$_2$(1,4-phe)Oc-Pr |

Assays for Determining Biological Activity

The leukotriene antagonist properties of the compounds of the present invention are evaluated using the following assays.

1. [$^3$H]LTD$_4$ Receptor Binding Assay in DMSO-differentiated U937 Cells (a human monocytic cell line);
2. [$^3$H]LTD$_4$ Receptor Binding on Guinea Pig Lung Membranes;
3. [$^3$H]LTD$_4$ Receptor Binding on Human Lung Membranes;
4. In Vitro Guinea Pig Trachea; and
5. In Vivo Assays in Anesthetized Guinea Pigs.

The above assays are described by T. R. Jones et al., Can. J. Physiol. Pharmacol. 1991, 69, 1847–1854.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carded out in a clear plastic box with internal dimensions 10×6×4 inches. The top of the box is removable; in use, it is held :firmly in place by four clamps and an airtight seal is maintained by a soft rubber gasket. Through the center of each end of the chamber a De Vilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a Buxco computer consisting of waveform analyzer, Data Acquisition Logger with special software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 nag aluminum hydroxide in saline. They are used between days 12 and 24 post sensitization. In order to eliminate the serotonin component of the response, rats are pretreated intravenously 5 minutes prior to aerosol challenge with 3.0 μg/kg of methysergide. Rats are then exposed to an aerosol of 3% EA in saline for exactly 1 minute, then their respiratory profiles are recorded for a further 30 minutes. The duration of continuous dyspnea is measured by the Buxco computer.

Compounds are generally administered either orally 2–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an ED50 is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or *Ascaris suum* antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28, 173–182 (1984) and McFarlane, C. S. et al., Agents Actions, 22, 63–68 (1987).)

Prevention of Induced Bronchoconstriction in Allergic Sheep

A. Rationale

Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods

Animal Preparation

Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.) and b) they have previously responded to inhalation challenge with *Ascaris suum* with both an acute bronchoconstriction and a late bronchial obstruction (W. M. Abraham et al., Am. Rev. Resp. Dis., 128, 839–44 (1983)).

Measurement of Airway Mechanics

The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Ca.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital s computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems

Aerosols of *Ascaris suum* extract (1:20) are generated using a disposable medicalnebulizer (Raindrop ®, Puritan Bennett), which produces an aerosol with a mass median aerodynamic diameter of 6.2 M (geometric standard deviation, 2.1 ) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol

Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5-1 hr prior to Ascaris challenge and for 8 hrs after Ascaris as described above.

Statistical Analysis

A Kruskal-Wallis one way ANOVA test is used to compare the acute immediate responses to antigen and the peak late response in the controls and the drug treated animals.

INTRODUCTION TO EXAMPLES

The invention will now be illustrated by the following non-limiting examples in which, unless stated otherwise:

(i) all operations were carded out at room or ambient temperature, that is, at a temperature in the range 18°–25° C.;

(ii) evaporation of solvent was carded out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry, or microanalytical data;

(vi) yields are given for illustration only;

(vii) when given, NMR data are in the form of delta (_) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram(s)), mg (milligram(s)), mol (moles), mmol (millimoles), eq (equivalent(s)).

EXAMPLE 1

Sodium (R) 1-(((1-(3-(2-(6-chlorothieno[3,2-d]thiazol-2-yl)ethenyl)-phenyl)-3-(2-(1-hydroxy-1-methylethyl)phenyl)-propyl)thio)methyl)cyclopropaneacetate Step 1

2-Methylthieno[3,2-d]thiazole

A solution of 660 mg (3.1 mmol) of N-acetyl-2-(acetylthio)-3-thiophenamine in 8 ml of toluene was degased in a pyrex tube under high vacuum. The tube was subsequently sealed under high vacuum and heated at 205° C. for 5 hr. Chromatographic separation on silica gel using hexane/EtOAc=5:1 gave 440 mg (80%) of product. $^1$H NMR (CDCl$_3$) 7.40(s, 2H), 2.82(s, 3H)

Step 2

6-chloro-2-methylthieno[3,2-d]thiazole

To a solution of 1.18 g (7.2 mmol) of 2-methyl-thieno[3.2-d]thiazole (from Step 1) in 35 ml of CH$_2$Cl$_2$ was added 670 mg (2.9 mmol) of trichloroisocyanuric acid at 0° C. The reaction was stirred at 0° C. for 30 min., then at r.t. for 2 h.; 60 mg (0.26 mmol) of trichloroisocyanuric acid was again added, and the reaction was stirred at r.t. for another hour. The product was partitioned between CH$_2$Cl$_2$ and aqueous NaHCO$_3$. Chromatographic purification on silica gel using hexane/EtOAc=5:1 afforded 1.2 g (90%) of the title product. $^1$H NMR (CDCl$_3$) 7.28(s, 1H), 2.82(s, 3H).

Step 3

2-(Bromomethyl)-6-chlorothieno[3,2-d]thiazole

To a solution of 310 mg(1.62 mmol) of 6-chloro-2-methylthieno[3,2-d]thiazole (from Step 2) and 10 mg of benzoyl peroxide in 15 ml of CC14 was added 306 mg(1.72 mmol) of NBS at r.t. The mixture was stirred at 75° C. under radiation from a sunlamp for 30 min. The solid was filtered, the solution was evaporated to dryness and the residue purified on silica gel with hexane/EtOAc=8:1 to give 300 mg (69%) of the title product. $^1$H NMR (CDCl$_3$) 7.35(s, 1H), 4.80(s,2H).

Step 4

((6-chlorothieno(3.2-d]thiazol-2-yl)methyl)triphenyl-phosphonium bromide

A solution of 300 mg (1.1 mmol) of 2-(bromomethyl)-6-chlorothieno[3.2-d1]thiazole (from Step 3) and 650 mg (2.4 mmol) of triphenylphosphine in 5 ml of acetonitrile was stirred at r.t. for 4 h. The product was precipitated from the solution with Et$_2$O, filtered and swished with Et$_2$O to give 400 mg (70%) of the title product. $^1$H NMR (DMSO-d6) 7.95–7.73(m, 16H), 5.91(d, J=14 Hz, 2H).

Step 5

1,1-Cyclopropanedimethanol cyclic sulfite

To a solution of BH$_3$.THF complex (1M in THF, 262 mL) was added diethyl 1,1-cyclopropanedicarboxylate (25 g, 134 mmol) at 25° C. under N$_2$. The solution was heated at reflux for 6 h, cooled to r.t., and MeOH (300 mL) was cautiously added. The solution was stirred for 1 h and then concentrated to an oil. The crude diol was dissolved in CH$_2$Cl$_2$ (234 mL) and SOCl$_2$ (15.9 g, 134 mmol) was added dropwise over a period of 15 min at 25° C. After stirring for another 15 min, the mixture was washed with aqueous NaHCO$_3$. The organic extract was dried over Na$_2$SO$_4$, filtered and concentrated to give quantitatively the title compound as a white solid.

Step 6

1-(Hydroxymethyl)cyclopropaneacetonitrile

To a solution of the cyclic sulfite product of step 5 (14.7 g, 99 mmol) in DMF (83 mL) was added NaCN (9.74 g, 199 mmol). The mixture was heated to 90° C. for 20 h. Upon cooling, EtOAc (400 mL) was added and the solution was washed with saturated NaHCO$_3$ solution (55 mL), H$_2$O (4×55mL), saturated NaCl solution and dried over Na$_2$SO$_4$. The solution was concentrated to give 7.1 g (65%) of the title compound.

Step 7

1-(Acetylthiomethyl)cyclopropaneacetonitrile

To a solution of the alcohol of Step 6 (42 g, 378 mmol) in dry CH$_2$Cl$_2$ (450 mL) at −30° C. was added Et$_3$N (103.7 mL, 741 mmol) followed by CH$_3$SO$_2$Cl (43.3 mL, 562 mmol) dropwise. The mixture was warmed to 25° C., washed with NaHCO$_3$, dried over Na$_2$SO$_4$ and concentrated in vacuo to give the corresponding mesylate. The mesylate was then dissolved in DMF (450 mL) and cooled to 0° C. Potassium thioacetate (55.4 g, 485 mmol) was added, and the mixture was stirred at 25° C. for 18 h. EtOAc (1.5 L) was added, the solution was washed with NaHCO$_3$, dried over Na$_2$SO$_4$ and concentrated in vacuo to give 45 g (70%) of the title compound.

Step 8

Methyl-(mercaptomethyl)cyclopropaneacetate

To a solution of the nitrile of Step 7 (45 g, 266 mmol) in MeOH (1.36 L) was added H$_2$O (84 mL) and conc. H$_2$SO$_4$ (168 mL). The mixture was heated to reflux for 20 h, cooled to 25° C., H$_2$O (1 L) was added and the product was extracted with CH$_2$Cl$_2$ (2×1.5 L). The organic extract was washed with H$_2$O and dried over Na$_2$SO$_4$. Concentration of the organic solution gave 36 g (93%) of the title compound.

Step 9

3-(((2-Tetrahydropyranyl)oxy)methyl)benzaldehyde

Isophthalaldehyde (150 g, 1.1 mole) was dissolved in THF (1 L) and EtOH (1 L) at 0° C. NaBH$_4$ (11.0 g, 291 mmol) was added portionwise and the mixture stirred 1 hour at 0° C. Addition of 25% aq. NH$_4$OAc and extraction with EtOAc (2×) followed by purification by flash chromatography (20% to 40% EtOAc in hexanes) yielded 60 g of 3-(hydroxymethyl)benzaldehyde.

This alcohol (0.44 mole) was dissolved in CH$_2$Cl$_2$ (500 ml). DHP (50 g, 0.59 mole) and PTSA (1 g, 5 mmol) were added and the mixture was stirred overnight at r.t. After concentration in vacuo, the residue was purified by flash chromatography (5% to 15% EtOAc in toluene) to give 85 g of the title compound.

Step 10

1-(3-(((2-Tetrahydropyranyl)oxy)methyl)phenyl)prop-2-ene-1-ol

To the aldehyde of Step 9 (85 g, 386 mmol) in toluene (1 L) at 0° C. was slowly added vinyl magnesium bromide in Et$_2$O (450 ml, 1 M, 450 mmol) over a 30 minute period. After stirring for 1 hour at 0° C., the reaction mixture was quenched with 25% aq. NH$_4$OAc and extracted with EtOAc (3×). Evaporation and purification by flash chromatography (15% to 25% EtOAc in toluene) yielded 82 g (86%) of the title compound.

Step 11

Ethyl 2-(3-(3-(((2-tetrahydropyranyl)oxy)methyl)phenyl)-3-oxopropyl)benzoate

The allylic alcohol of Step 10 (24.8 g, 100 mmol) and ethyl 2-bromobenzoate (25.2 g, 110 mmol) were dissolved in DMF (200 mL). LiCl (4.2 g, 100 mmol), LiOAc.2H$_2$O (25.5 g, 250 mmol) and n-Bu$_4$N+Cl− (55 g, 200 mmol) were added and the resulting mixture was degassed three times. Pd(OAc)$_2$ (1 g) was then added and the mixture was degassed three more times before heating it at 100° C. with stirring for 1 hour. After cooling to r.t., the reaction mixture was poured onto H$_2$O (600 mL), 10% aq. NaHCO$_3$ (200 mL) and Et$_2$O. The crude product was extracted with Et$_2$O (2×), washed with H$_2$O and brine, and dried over Na$_2$SO$_4$ before concentrating in vacuo. Purification on a short silica gel column (20% EtOAc in hexanes) gave 34 g (86%) of the title compound. $^1$H NMR (CD$_3$COCD$_3$): δ8.02 (1H, br s), 7.92 (1H, d), 7.88 (1H, d), 7.65 (1H, d), 7.50 (3H, m), 7.32 (1H, br t), 4.8 (1H, d), 4.70 (1H, br s), 4.54 (1H, d), 4.3 (2H, q), 3.82 (1H, m), 3.50 (1H, m), 3.35 (2H, m), 1.9–1.45 (8H, m), 1.32 (3H, t).

Step 12

Ethyl 2-(3(S)-hydroxy-3-(3-(((2-tetrahydropyranyl)oxy)methyl)phenyl)propyl benzoate The ketoester of Step 11 (24.8 g, 62.5 mmol) was dissolved in THF (230 mL) and cooled to -45° C. A THF (15 ml) solution of tetrahydro-1-methyl-3,3-diphenyl-1H,3H-pyrrolo[1,2-c][1,3,2]oxazoborole.borane adduct (J. Org. Chem. 56, 751 (1991), 4.55 g, 15.6 mmol) was added dropwise and the resulting mixture was stirred 20 minutes at −45° C. To this solution, 1.0M borane in THF (62.5 mL, 62.5 mmol) was added dropwise over 30 minutes. The reaction mixture was stirred 1 hour at −45° C. followed by another 2 hours with slow warming to −20° C. After cooling the solution to −40° C., it was poured onto 25% aq. NH$_4$OAc (425 mL) and 1.0 M diethanolamine (40 mL) at 0° C. and stirred vigorously for 20 minutes. The title compound was extracted with EtOAc (3×), dried over MgSO$_4$ and concentrated under reduced pressure. The crude oil was purified by flash chromatography (25% to 50% EtOAc in hexanes) to yield 22.6 g (91%) of the title product as an oil. [α]$_D^{25}$ = −32.6° (c=3, CHCl$_3$)

Step 13

1(S)-(3-(((2-Tetrahydropyranyl)oxy)methyl)phenyl)-3-(2-(1-hydroxy-1-methylethyl)phenyl)propan-1-ol Anhydrous CeCl$_3$ (17.25 g, 70 mmol) was refluxed for 2.5 hours in THF (200 ml) using a Dean-Stark trap filled with molecular sieves to remove H$_2$O. The ivory suspension was cooled to −5° C. and MeMgCl(114 mL, 3 M in THF, 340 mmol) was added dropwise while keeping the internal temperature between −10° C. and 0° C. The grey suspension was stirred 2 hours before slowly adding to it the hydroxyester of step 12 (27.1 g, 68 mmol) as a THF solution (200 mL) via a cannula. The resulting mixture was stirred 1.5 hours at or below 0° C., and then slowly poured onto ice cold 1M HOAc (1 L) and EtOAc (500 ml) and stirred for 30 minutes. After adjusting the pH to 6–7, the crude compound was extracted with EtOAc (2×) and the combined organic phases were washed with saturated aq. NaHCO$_3$ followed with brine. Purification on a short silica gel column (30% to 50% EtOAc in hexanes) yielded 24.5 g (95%) of the title compound.

Step 14

Methyl
1-(((1(R)-(3-(((2-tetrahydropyranyl)oxy)methyl)-
phenyl)-3-(2-(1-hydroxy-1-methylethyl)phenyl)-
propyl)thio)methyl)cyclopropaneacetate The diol of Step 13 (17.9 g, 46.6 mmol) was dissolved in CH$_3$CN (40 mL) and DMF (10 mL) and cooled to −42° C. under nitrogen. Diisopropylethylamine (8.5 mL, 48.9 mmol) was added followed by methanesulfonyl chloride (3.6 mL, 46.6 mmol) dropwise. The solution was stirred 1.5 hours with a mechanical stirring while maintaining the temperature between −42° and −35° C.; then it was cooled to −45° C. The thiol of Step 8 (7.84 g, 48.9 mmol) was added followed by dropwise addition of DMF (15 mL). Potassium tert-butoxide in THF (56 mL, 1.75 M, 97.9 mmol) was added to the reaction mixture over 20 minutes using a syringe pump. Stirring was continued for 5 hours with slow warming from −35° C. to −22° C., giving a very thick translucid gel. The reaction was quenched with saturated aq. NH$_4$Cl (250 mL) and EtOAc (300 mL). The product was extracted with EtOAc, washed with H$_2$O and brine, and dried over MgSO4. Purification by flash chromatography (20% to 30% EtOAc in hexanes) gave 16.8 g (68%) of the title compound.

Step 15

Methyl
1-(((1(R)-(3-(hydroxymethyl)phenyl)-3-(2-(1-hydroxy-
1-methylethyl)phenyl)propyl)thio)methyl)cyclopro-
paneacetate To the hydroxy ester from Step 14 (9.02 g, 17.1 mol) in anhydrous MeOH (60 mL) under nitrogen was added pyridine (50 μL) followed by PPTS (1.1 g, 4.3 mmol). The reaction mixture was stirred 3.5 hours at 55° C., then at r.t. overnight before concentrating in vacuo. The residue was diluted with EtOAc (500 mL) and washed with H$_2$O, saturated aq. NaHCO$_3$, NaH$_2$PO$_4$ buffer (pH=4.5) and with brine. After drying over MgSO$_4$ and evaporation of the solvents, the residue was purified by flash chromatography (40% to 60% EtOAc in hexanes) giving 6.85 g (91%) of the title compound. $^1$H NMR (CD$_3$COCD$_3$): δ5 7.41 (2H, m), 7.27 (3H, m), 7.09 (3H, m), 4.63 (2H, d), 4.19 (1H, t), 3.95 (1H, t), 3.88 (1H, s), 3.57 (3H, s), 3.1 (1H, ddd), 2.8 (1H, ddd), 2.5 (2H, s), 2.4 (2H, d), 2.17 (2H, m), 1.52 (6H, s), 0.52–0.35 (4H, m).

Step 16

Methyl 1-(((1
(R)-(3-formylphenyl)-3-(2-(1-hydroxy-1-methylethyl)-
phenyl)propyl)thio)methyl)cyclopropaneacetate To the dihydroxy ester from Step 15 (6.8 g, 15.4 mmol) in EtOAc (150 mL) at 50° C. was added MnO$_2$ (6.7 g, 76.8 mmol). After stirring for 30 minutes at 50° C. more MnO$_2$ (6.7 g) was added, and 30 minutes later, a third portion of MnO$_2$ (6.7 g) was added. An hour later, the warm reaction mixture was filtered through celite and the cake was washed with additional EtOAc. Evaporation of the solvents gave the title aldehyde 5.62 g (83%). $^1$H NMR (CD$_3$COCD$_3$): δ5 10.4 (1H, s), 7.9 (1H, br s), 7.8 (2H, m), 7.58 (1H, t), 7.38 (1H, br d), 7.1 (3H, m), 4.1 (1H, t), 3.54 (3H, s), 3.13 (1H, ddd), 2.85 (1H, ddd), 2.51 (2H, s), 2.49 (2H, d), 2.2 (2H, m), 1.51 (6H, s), 0.52–0.32 (4H, m).

Step 17

Methyl (R)
1-(((1-(3-(2-(6-chlorothieno[3,2-d]thiazol-2-yl)ethenyl)-
phenyl)-3-(2-(1-hydroxy-1-methylethyl)phenyl)-
propyl)thio)methyl)cyclopropaneacetate To a suspension of the phosphonium salt from Step 4 (310 mg, 0.58 mmol) in THF (8 mL) was added 1.22 mL (0.61 mmol) of KHMDS (0.5M in toluene) at −78° C. The mixture was warmed up to 0° C. for 15 min, and then cooled to −78° C., to which was added the aldehyde from Step 16 (250 mg, 0.58 mmol) at −78° C. The mixture was stirred at −78° C. for 15 min, warmed up to 0° C. for 2 hr, and then at r.t. for 1 hr. Aqueous NH$_4$OAc was added and the mixture was extracted with EtOAc. The organic extract was washed with brine, dried over MgSO$_4$ and concentrated to an oil. Chromatography of the crude oil on silica gel (eluted with 20% EtOAc in hexane) gave 420 mg (98%) of the title compound. 1H NMR (CDCl$_3$): δ5 7.54(s, 1H), 7.42(m, 2H), 7.39–7.31 (m, 5H), 7.20–7.08(m, 3H), 3.92(t, J=7.2 Hz, 1H), 3.60(s, 3H), 3.19–3.08(m, 1H), 2.90–2.79(m, 1H), 2.48(s, 2H), 2.40(s, 2H), 2.28–2.08(m, 2H), 1.61(s, 3H), 1.59(s, 3H), 0.55–0.38(m, 4H).

Step 18

Sodium (R)
1-(((1-(3-(2-(6-chlorothieno[3,2-d]thiazol-2-yl)ethenyl)-
phenyl)-3-(2-(1-hydroxy-1-methylethyl)phenyl)-
propyl)thio)methyl)cyclopropaneacetate To a solution of the ester of Step 17 in THF (1 mL) and MeOH (1 mL) was added aqueous NaOH (1N, 1.4 mL). The mixture was stirred at 25° C. for 20 h., NH$_4$Cl was added and the mixture was extracted with EtOAc. The organic extract was washed with brine, dried over MgSO$_4$ and concentrated to an oil. Chromatography of the crude oil on silica gel. (eluted with 20% EtOAc / 5% HOAc in hexane) gave 330 mg (79%) of the corresponding acid. To this acid in 3 mL EtOH was added NaOH (1N, 1.0 equivalent). The solvent was evaporated and the product was lyopholyzed to give the title compound. $^1$H NMR (CDCl$_3$): δ7.57(s, 1H), 7.43–7.08(m, 10H), 3.98(t, J=7.2 Hz, 1H), 3.25–3.12(m, 1H), 2.94–2.81(m, 1H), 2.55(d, J=15 Hz, 1H), 2.40(d, J=15 Hz, 1H), 2.41(s, 2H), 2.25–2.10(m, 2H), 1.65(s, 3H), 1.61(s, 3H), 0.65–0.38(m, 4H).

EXAMPLE 2

Sodium (R)
1-(((1-(3-(2-(5,6-dichlorothieno[3,2-d]thiazol-2-yl)e-
thenyl)phenyl)-3-(2-(1-hydroxy-1-methylethyl)phenyl)-
propyl)thio)methyl)cyclopropaneacetate

Step 1

5,6-dichloro-2-methylthjeno[3,2-d]thiazole

At −100° C., a solution of LDA (4.06 mmol) in 10 ml of THF was added dropwise to a solution of 6-chloro-2-methylthieno[3,2-d]thiazole (Example 1, Step 2; 665 mg, 3.51 mmol) in 10 ml of THF over 5 min. and the mixture was stirred at −100° C. for 5 min. A solution of NCS (720 mg, 5.27 mmol) in 14 ml of THF was then added and the mixture was stirred at −78° C. for 15 min. 25% Aq. NH$_4$OAc was then added and the product was extracted in EtOAc, dried over Na$_2$SO$_4$ and purified by HPLC on a Zorbax column with EtOAc:-toluene 2.5:97.5 to give the title product and some remaining starting material. $^1$H NMR (CDCl$_3$) δ2.86(3H, s)

Step 2

Sodium (R) 1-(((1-(3-(2-(5,6-dichlorothieno[3,2-d]thiazol-2-yl)ethenyl)phenyl)-3-(2-(1-hydroxy-1-methylethyl)phenyl)propyl)thio)methyl)cyclopropaneacetate Following the procedure described in Steps 3-18 of Example 1, but using the compound of Step 1 of this Example, the title compound was prepared. $^1$H NMR (CDCl$_3$) of the acid. δ5 7.60(1H, s), 7.50-7.30(6H, m), 7.20-7.05(3H, m), 4.00(1 H, t), 3.20(1 H, m), 2.89(1H, m), 2.48(1H, d, J=13 Hz), 2.45-2.35(3H, m), 2.18(2H, m), 1.65(3H, s), 1.62(3H, s), 0.62(1H, m), 0.50(2H, m), 0.40(1H, m). Anal. calcd for C$_{31}$H$_{30}$Cl$_2$NO$_3$S$_3$Na.H$_2$O: C, 5.5.35; H, 4.79; N, 2.08. Found: C, 55.40; H, 5.01; N, 1.72.

What is claimed is:

1. A compound of the formula:

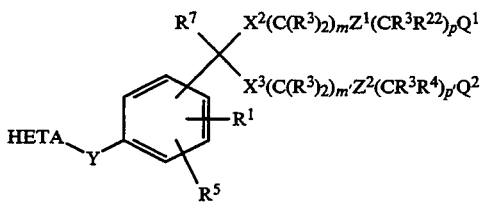

wherein:

R$^1$ is H or R$^2$;

R$^2$ is lower alkyl, lower alkenyl, lower alkynyl, fluoro lower alkyl, Ph(R$^{26}$)$_2$, CH$_2$Ph(R$^{26}$)$_2$, CH$_2$CH$_2$Ph(R$^{26}$)$_2$ or two R$^2$ groups joined to the same carbon can form a ring of up to 8 members containing up to 2 heteroatoms chosen from O,S, and N;

R$^3$ is H or R$^2$;

R$^4$ is R$^3$, halogen, —NO$_2$, —CN, —CF$_3$, —OR$^3$, N(R$^3$)$_2$, NR$^3$COR$^7$, —SR$^2$, S(O)R$^2$ or S(O)$_2$R$^2$;

CR$^3$R$^{22}$ can be the radical of a conventional amino acid;

R$^5$ is H, halogen, —NO$_2$, —N$_3$, —CN, —SR$^2$, —S(O)R$^2$, S(O)$_2$R$^2$, —N(R$^{10}$)$_2$, —OR$^3$, —COR$^3$, lower alkyl or fluoro lower alkyl;

R$^6$ is —(CH$_2$)$_s$—C(R$^7$)$_2$—(CH$_2$)$_s$—R$^8$ or —CH$_2$CON(R$^{20}$)$_2$;

R$^7$ is H or lower alkyl;

R$^8$ is A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or B) the radical W—R$^9$;

R$^9$ contains up to 21 carbon atoms and is (1) a hydrocarbon radical or (2) an acyl radical of an organic acyclic or monocyclic carboxylic acid containing not more than 1 heteroatom in the ring;

R$^{10}$ is R$^{12}$;

R$^{11}$ is lower alkyl, —COR$^{14}$, Ph(R$^{26}$)$_2$, CH$_2$Ph(R$^{26}$)$_2$ CH$_2$CH$_2$Ph(R$^{26}$)$_2$;

R$^{12}$ is H, R$^{11}$, or two R$^{12}$ groups joined to the same N can form a saturated ring of 5 or 6 members containing up to two heteroatoms chosen from O, S, and N;

R$^{13}$ is lower alkyl, lower alkenyl, lower alkynyl, —CF$_3$, Ph(R$^{26}$)$_2$, CH$_2$Ph(R$^{26}$)$_2$ or CH$_2$CH$_2$Ph(R$^{26}$)$_2$;

R$^{14}$ is H or R$^{13}$;

R$^{15}$ is H or R$^{11}$;

R$^{16}$ is H, lower alkyl, or OH;

R$^{17}$ is lower alkyl, lower alkenyl, lower alkynyl, Ph(R$^{26}$)$_2$, CH$_2$Ph(R$^{26}$)$_2$ or CH$_2$CH$_2$Ph(R$^{26}$)$_2$;

R$^{18}$ is R$^{13}$;

R$^{19}$ is H, lower alkyl, lower alkenyl, lower alkynyl, —CF$_3$, Ph, CH$_2$Ph, or CH$_2$CH$_2$Ph;

R$^{20}$ is H, lower alkyl, Ph(R$^{26}$)$_2$, CH$_2$Ph(R$^{26}$)$_2$, CH$_2$CH$_2$Ph(R$^{26}$)$_2$ or two R$^{20}$ groups joined to the same N can form a saturated ring of 5 or 6 members containing up to two heteroatoms chosen from O, S, and N;

R$^{21}$ is H or R$^{17}$;

R$^{22}$ is R$^4$, CHR$^7$OR$^3$ or CHR$^7$SR$^2$;

R$^{23}$, R$^{24}$ and R$^{25}$ are each independently H, lower alkyl, —CN, —CF$_3$, COR$^3$, CO$_2$R$^7$, CON(R$^{20}$)$_2$, OR$^3$, SR$^2$, S(O)R$^2$, S(O)$_2$R$^2$, N(R$^{12}$)$_2$, halogen, or an electron pair;

R$^{26}$ is H, lower alkyl, —COR$^7$, CO$_2$R$^7$, CON(R$^{19}$)$_2$, —CN, CF$_3$, NO$_2$, SCF$_3$, SR$^{27}$, OR$^{28}$, N(R$^{28}$)$_2$, or halogen;

R$^{27}$ is lower alkyl, phenyl or benzyl;

R$^{28}$ is H, R$^{27}$ or COR$^7$, or two R$^{28}$ groups joined to the same N can form a saturated ring of 5 or 6 members comprising carbon atoms and up to 2 heteroatoms chosen from O, S or N;

m and m' are independently 0-8;

p and p' are independently 0-8;

m+p is 1-10 when X$^2$ is O, S, S(O), or S(O)$_2$ and Z$^1$ is a bond;

m+p is 0-10 when Z$^1$ is HET(R$^{23}$R$^{24}$R$^{25}$);

m+p is 0-10 when X$^2$ is CR$^3$R$^{16}$;

m'+p' is 1-10 when X$^3$ is O, S, S(O), or S(O)$_2$ and Z$^2$ is a bond;

m'+p' is 0-10 when Z$^2$ is HET(R$^{23}$R$^{24}$R$^{25}$);

m'+p' is 0-10 when X$^3$ is CR$^3$R$^{16}$;

s is 0-3;

Q$^1$ is tetrazol-5-yl, —CO$_2$R$^3$, —CO$_2$R$^6$, —CONHS(O)$_2$R$^{13}$, —CN, —CON(R$^{20}$)$_2$, NR$^{21}$S(O)$_2$R$^{13}$, —NR$^{21}$CON(R$^{20}$)$_2$, —NR$^{21}$COR$^{14}$, OCON(R$^{20}$)$_2$, —COR$^{19}$, —S(O)R$^{18}$, —S(O)$_2$R$^{18}$, —S(O)$_2$N(R$^{12}$)$_2$, —NO$_2$, NR$^{21}$CO$_2$R$^{17}$, —C(N(R$^{12}$)$_2$)=NR$^{21}$, —C(R$^{19}$)=NOH, C(R$^3$)$_2$OR$^3$; or if Q$^1$ is CO$_2$H and R$^{22}$ is —OH, —SH, CHR$^7$OH or —NHR$^3$, then Q$^1$ and R$^{22}$ and the carbons through which they are attached can form a heterocyclic ring by loss of water;

Q$^2$ is H, OR$^{15}$, lower alkyl, fluoro lower alkyl, halogen or Q$^1$;

W is O, S, or NR$^3$;

X$^1$ is O, S, —S(O)—, —S(O)$_2$—,—NR$^3$, —C(R$^3$)$_2$—, or a bond;

X$^2$ and X$^3$ are independently O, S, S(O), S(O)$_2$, CR$^3$R$^{16}$ or a bond;

Y is —CR$^3$=CR$^3$—, —C(R$^3$)$_2$—X$^1$—, —X$^1$—C(R$^3$)$_2$—, —C(R$^3$)$_2$—X$^1$—C(R$^3$)$_2$—, —C≡C—, —CO—, —NR$^3$CO—, —CONR$^3$—, O, S, or NR$^3$;

Z$^1$ and Z$^2$ are independently HET(R$^{23}$R$^{24}$R$^{25}$) or a bond;

HET is the diradical of benzene, pyridine, furan, thiophene or 1,2,5-thiadiazole;

HETA is HE$^1$ or HE$^2$; wherein

HE$^1$ is

HE² is

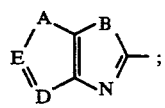

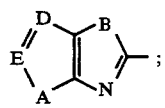

each A is O, S, S(O)₂;
each B is independently O, S, S(O) or S(O)₂;
each D is independently N or CR⁴;
E is CR4 except when D is N, then E is CR3; or a pharmaceutically acceptable salt thereof.

2. A compound of claim 1 of the formula:

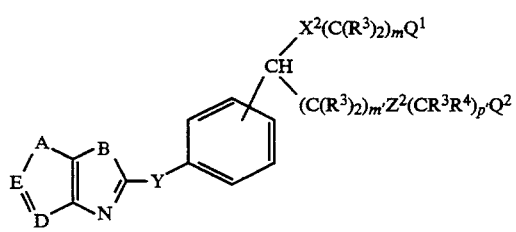

wherein:
A is S or O;
B is S or O;
R⁴ is H, halogen, CN, CF₃, or S(O)₂R²;
m and m' are each independently 1-6;
p' is 0 or 1;
Q1 is CO₂R³, CO₂R⁶, —CONHS(O)₂R¹³, tetrazol-5-yl, or C(R³)₂OH;
Q² is C(R³)₂OH, halogen, lower alkyl or COR¹⁹;
X² is S or O;
Y is —CH=CH—, —CH₂—O—, —CH₂—CH₂—, —C≡C— or —CH(CH₂)CH—;
Z² is HET (R²³R²⁴); and
HET is a diradical of benzene or thiophene.

3. A compound of claim 2 of the formula:

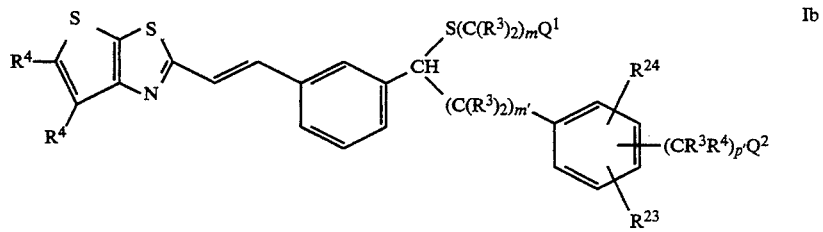

wherein:
R³ is H, lower alkyl, or two R³ joined to the same carbon may form a ring from 3 to 6 members, optionally containing one oxygen or sulfur;
R⁴ is H, halogen, —CN, —CF₃, —S(O)₂R²;
R²³ and R²⁴ are independently H, halogen or lower alkyl;
m and m' are independently 1-5;
p' is 0 or 1;
Q¹ is —CO₂R³, tetrazol-5-yl, or —CONHS(O)₂R¹³; and
Q² is H, C(R³)₂OH; or OR¹⁵.

4. A compound of claim 1 of the formula:

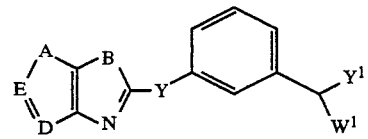

wherein the substituents are defined in the following Table 1:

TABLE 1

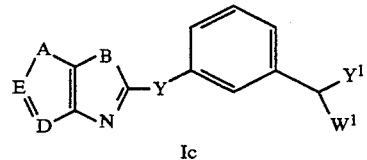

| EX | A | B | D | E | Y | Y¹ | W¹ |
|---|---|---|---|---|---|---|---|
| 1 | S | S | CCl | CH | CH=CH | SCH₂(1,1-c-Pr)CH₂CO₂H | (CH₂)₂(1,2-phe)C(CH₃)₂OH |
| 2 | S | S | CCl | CCl | CH=CH | SCH₂(1,1-c-Pr)CH₂CO₂H | (CH₂)₂(1,2-phe)C(CH₃)₂OH |
| 3 | S | S | CH | CCl | CH=CH | SCH₂(1,1-c-Pr)CH₂CO₂H | (CH₂)₂(1,2-phe)C(CH₃)₂OH |
| 4 | S | O | CH | CCl | CH=CH | SCH₂(1,1-c-Pr)CH₂CO₂H | (CH₂)₂(1,2-phe)C(CH₃)₂OH |
| 5 | S | S | CH | CF | CH=CH | SCH₂(1,1-c-Pr)CH₂CO₂H | (CH₂)₂(1,2-phe)C(CH₃)₂OH |
| 6 | S | S | CF | CF | CH=CH | SCH₂(1,1-c-Pr)CH₂CO₂H | (CH₂)₂(1,2-phe)C(CH₃)₂OH |
| 7 | S | S | CH | CCF₃ | CH=CH | SCH₂(1,1-c-Pr)CH₂CO₂H | (CH₂)₂(1,2-phe)C(CH₃)₂OH |
| 9 | S | S | CCl | CH | CH=CH | SCH₂(1,1-c-Pr)CH₂CO₂H | (CH₂)₂(1,3-phe)C(CH₃)₂OH |
| 10 | O | S | CH | CCl | CH=CH | SCH₂(1,1-c-Pr)CH₂CO₂H | (CH₂)₂(1,2-phe)C(CH₃)₂OH |
| 11 | S | S | CCl | CF | CH=CH | SCH₂(1,1-c-Pr)CH₂CO₂H | (CH₂)₂(1,2-phe)C(CH₃)₂OH |
| 12 | S | S | CCl | CCl | CH=CH | SCH₂(1,1-c-Pr)CH₂CO₂H | (CH₂)₂(1,4-phe)c-Pr |
| 13 | S | S | CCl | CH | CH=CH | SCH₂(1,1-c-Pr)CH₂CO₂H | (CH₂)₂(1,4-phe)c-Pr |
| 14 | S | S | CH | CCl | CH=CH | SCH₂(1,1-c-Pr)CH₂CO₂H | (CH₂)₂(1,4-phe)c-Pr |
| 15 | S | S | CH | CCl | CH=CH | SCH₂(1,1-c-Pr)CH₂CO₂H | (CH₂)₂(1,4-phe)-O-c-Pr |
| 16 | S | S | CH | CF | CH=CH | SCH₂(1,1-c-Pr)CH₂CO₂H | (CH₂)₂(1,4-phe)c-Pr |
| 17 | S | S | CF | CF | CH=CH | SCH₂(1,1-c-Pr)CH₂CO₂H | (CH₂)₂(1,4-phe)c-Pr |

TABLE 1-continued

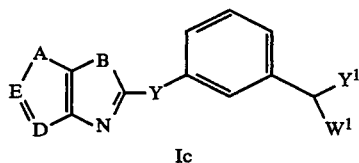

Ic

| EX | A | B | D | E | Y | Y¹ | W¹ |
|---|---|---|---|---|---|---|---|
| 18 | S | S | CH | CCF$_3$ | CH=CH | SCH$_2$(1,1-c-Pr)CH$_2$CO$_2$H | (CH$_2$)$_2$(1,4-phe)c-Pr |
| 20 | S | O | CCl | CH | CH=CH | SCH$_2$(1,1-c-Pr)CH$_2$CO$_2$H | (CH$_2$)$_2$(1,4-phe)c-Pr |
| 21 | S | O | CH | CCl | CH=CH | SCH$_2$(1,1-c-Pr)CH$_2$CO$_2$H | (CH$_2$)$_2$(1,4-phe)c-Pr |
| 22 | S | O | CF | CF | CH=CH | SCH$_2$(1,1-c-Pr)CH$_2$CO$_2$H | (CH$_2$)$_2$(1,4-phe)c-Pr |

5. A compound of claim 1 of the formula:

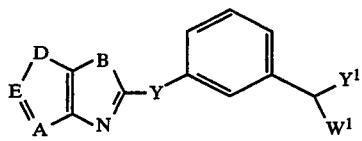

Id wherein the substituents are defined in the following Table 2:

TABLE 2

| EX | A | B | D | E | Y | Y¹ | W¹ |
|---|---|---|---|---|---|---|---|
| 23 | S | S | CCl | CH | CH=CH | SCH$_2$(1,1-c-Pr)CH$_2$CO$_2$H | (CH$_2$)$_2$(1,2-phe)C(CH$_3$)$_2$OH |
| 24 | S | S | CCl | CCF$_3$ | CH=CH | SCH$_2$(1,1-c-Pr)CH$_2$CO$_2$H | (CH$_2$)$_2$(1,2-phe)C(CH$_3$)$_2$OH |
| 25 | S | S | CCl | Cc—Pr | CH=CH | SCH$_2$(1,1-c-Pr)CH$_2$CO$_2$H | (CH$_2$)$_2$(1,2-phe)C(CH$_3$)$_2$OH |
| 26 | S | S | CCl | Cc—Pr | CH=CH | SCH$_2$C(CH$_3$)$_2$CH$_2$CO$_2$H | (CH$_2$)$_2$(1,2-phe)C(CH$_3$)$_2$OH |
| 27 | S | S | CCl | Cc—Pr | CH=CH | SCH$_2$C(CH$_3$)$_2$CH$_2$CO$_2$H | (CH$_2$)$_2$(1,4-phe)c-Pr |
| 28 | S | S | CCl | Cc—Pr | CH=CH | SCH$_2$(1,1-c-Pr)CH$_2$CO$_2$H | (CH$_2$)$_2$(1,4-phe)Br |
| 29 | S | S | CCl | Cc—Pr | CH=CH | SCH$_2$(1,1-c-Pr)CH$_2$CO$_2$H | (CH$_2$)$_2$(1,4-phe)Oc-Pr |

6. A pharmaceutical composition comprising a therapeutically effective amount of a compound of claim 1 and a pharmaceutically acceptable carder.

7. The pharmaceutical composition of claim 6 additionally comprising an effective amount of a second active ingredients selected from the group consisting of non-steroidal anti-inflammatory drugs; peripheral analgesic agents; cycloxygenase inhibitors; leukotriene antagonists; leukotriene biosynthesis inhibitors; H$_1$- or H$_2$-receptor antagonists; antihistaminic agents; prostaglandin antagonists; and ACE antagonists.

8. A pharmaceutical composition of claim 7, wherein the second active ingredient is non-steroidal anti-inflammatory drug.

9. A pharmaceutical composition of claim 8, wherein the weight ratio of said compound of claim 1 is said second active ingredient ranges from about 1000:1 to 1:1000.

10. A method of preventing the action of leukotrienes in a mammal which comprises administering to said mammal an effective amount of a compound of claim 1.

11. The method of claim 10 wherein the mammal is man.

12. A method of treating asthma in a mammal comprising administering to a mammal in need of such treatment a therapeutically effective amount of a compound of claim 1.

13. The method of claim 10 wherein the mammal is man.

14. A method of treating inflammatory diseases of the eye in mammal which comprises administering to a mammal in need of such treatment a therapeutically effective amount of a compound of claim 1.

* * * * *